(12) United States Patent
Douillet

(10) Patent No.: US 6,589,524 B1
(45) Date of Patent: Jul. 8, 2003

(54) STRAINS OF BACILLUS FOR BIOLOGICAL CONTROL OF PATHOGENIC FUNGI

(75) Inventor: Philippe Douillet, Miami, FL (US)

(73) Assignee: EcoMicrobials, LLC, Coconut Grove, FL (US)

( * ) Notice: Subject to any disclaimer, the term of this patent is extended or adjusted under 35 U.S.C. 154(b) by 0 days.

(21) Appl. No.: 10/072,030

(22) Filed: Feb. 7, 2002

(51) Int. Cl.[7] .................. A01N 25/00; A01N 63/00; C07G 17/00; C12N 1/00; C12N 1/20
(52) U.S. Cl. .................. 424/93.462; 424/93.46; 424/405; 435/252.4; 435/252.5; 435/267; 435/834; 435/839
(58) Field of Search .................. 210/600, 610, 210/601; 424/93.1, 246.1, 93.46, 93.462, 93.3, 405; 435/252.31, 252.5, 834, 252.4, 839, 267

(56) References Cited

U.S. PATENT DOCUMENTS

| | | |
|---|---|---|
| 4,764,371 A | 8/1988 | Pusey et al. |
| 5,470,827 A | 11/1995 | Tanaka et al. |
| 5,552,138 A | 9/1996 | Handelsman et al. |
| 5,700,462 A | 12/1997 | Handelsman et al. |
| 5,767,090 A | 6/1998 | Stanghellini et al. |
| 5,770,696 A | 6/1998 | Warren et al. |
| 5,830,459 A | 11/1998 | Cuero et al. |
| 5,994,117 A | 11/1999 | Bacon et al. |
| 6,034,124 A | 3/2000 | Handelsman et al. |
| 6,103,228 A | 8/2000 | Heins et al. |
| 6,133,196 A | 10/2000 | Ocamb et al. |
| 6,194,193 B1 | 2/2001 | Drahos et al. |
| 6,291,426 B1 * | 9/2001 | Heins et al. .................. 514/9 |

OTHER PUBLICATIONS

Broadbent et al., 1971, *Austral. J. Biol. Sci.* 24:925–944.
Jones and Ehret, 1976, *Plant Dis. Rep.* 60:765–769.
Katz and Demain, 1977, *Bacteriol. Rev.* 41:449–474.
McKeen et al., 1986, *Phytopathology* 76(2):136–139.
Utkhede and Sholberg, 1986, *Can. J. Microbiol.* 32:963–967.
Guelder et al., 1988, *J. Agric. Food Chem.* 36: 366–370.
Stabb et al., 1990, *Applied Environ. Microbiol.* 60(12):4404–4412.
Ferrin, 1992, *Plant Disease*, 76:60–63, p. 82–84.
Whipps, 1994, Advances in Biological Control in Protected Crops, Brighton Crop Prot. Conf. Pest Dis. 9B:1259–1264.
Berger et al., 1996, *Phytopathology* 86(5):428–433.
Asaka and Shoda, 1996, *Appl. Env. Microbiol.* 62(11):4081–4085.

* cited by examiner

Primary Examiner—David M. Naff
Assistant Examiner—Deborah K. Ware
(74) Attorney, Agent, or Firm—Saliwanchik, Lloyd & Saliwanchik

(57) ABSTRACT

Biological control composition comprising specific strains of Bacillus, which are selected from the group of *Bacillus cereus* NRRL B-30517 and NRRL B-30519, *Bacillus amyloliquefaciens* NRRL B-30518 and *Bacillus subtilis* NRRL B-30520, as well as a method therefore are provided. Furthermore, the specific strains in combination provide a synergistic effect against pathogenic fungi. The pathogenic fungi include varied Phytophthora species such as *P. capsici*.

16 Claims, 7 Drawing Sheets

STRAINS OF BACILLUS FOR BIOLOGICAL CONTROL OF PATHOGENIC FUNGI

BACKGROUND OF THE INVENTION

1. Field of the Invention

Figure 1:
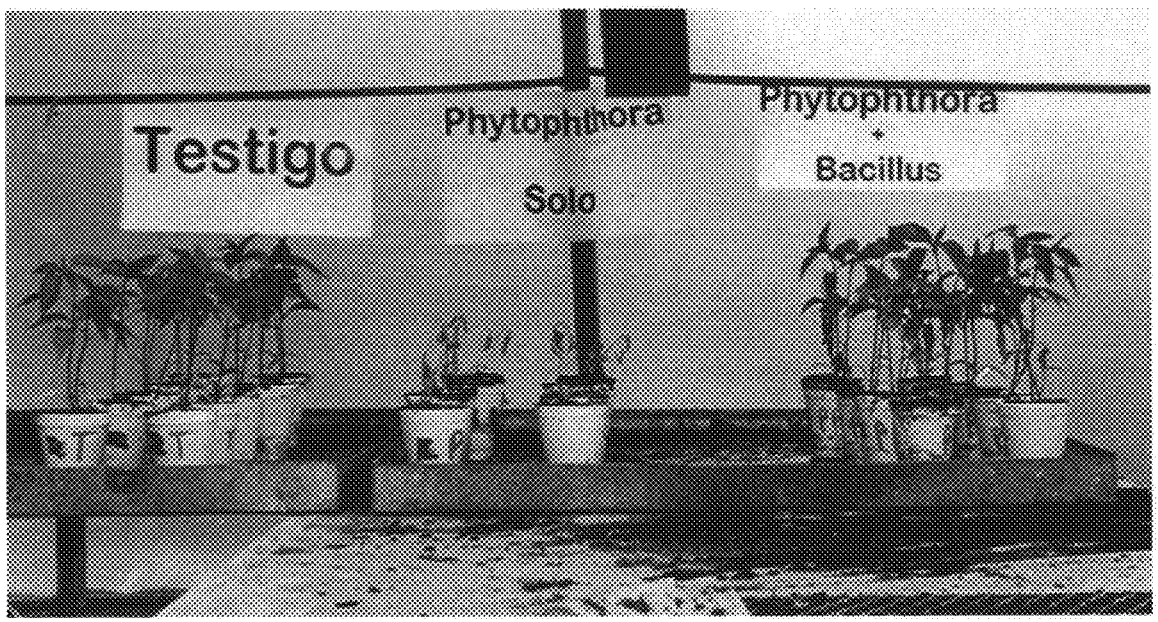

This invention relates to biological methods and products useful in agriculture. More specifically, the present invention is directed to a method for controlling fungal diseases in plants.

2. Description of the Prior Art

Fungal diseases cause great economic damage to agricultural and ornamental crops around the world. Currently, most of the pesticides in use for control of fungal diseases are synthetic compounds. Many of these chemical fungicides are classified as carcinogens by the EPA, and are toxic to humans, wildlife, and other non-target species. In addition, many reports indicate that chemical fungicides have become less effective due to the development of pathogen resistance. (Schwinn et al. 1991, Advances in plant pathology: *Phytophthora infestans*, the cause of late blight of potato, Academic Press, San Diego; Jones and Ehret, 1976, *Plant Dis. Rep.* 60:765–769; Ferrin, 1992, *Plant Disease*, 76:60–63, p. 82–84). Alarm resulting from the growing incidence of pesticide resistance has prompted global efforts directed toward the search for alternative pest control strategies. One such strategy is biological control with antagonistic microorganisms or microbial products to directly or indirectly control target pests. See, for example, Stanghellini et al. 1998, U.S. Pat. No. 5,767,090. Biological control can be safer for humans and the environment, and less expensive to develop than chemical pesticides.

Screening programs have identified certain bacterial strains that exhibit antifungal activities. (Stabb et al. 1990, *Applied Environ. Microbiol.* 60(12):4404–4412; Broadbent et al. 1971, *Austral. J Biol. Sci.* 24:925–944; Baker et al. 1982, Biological control of plant pathogens, American Phytopathological Society, St. Paul, Minn., 433 pp). One of the mechanisms of bacterial antagonism to fungi is antibiosis, which consists in the inhibition or destruction of one organism by a metabolic product of another. Antibiosis can occur by at least three distinct mechanisms. First, it can occur by way of hydrolytic cell wall-degrading enzymes such as xylanases, mannanases, cellulases, proteases, and chitinases. Second, it can manifest as an enzyme that decreases fungal osmotolerance such as trehalase. Third, it can occur by the administration and activity of antibiotics.

The term antibiotic is very broad and includes widely disparate mechanisms. For example, penicillin interferes with cell wall formation, streptomycin interferes with protein synthesis; and siderophores are compounds that inhibit growth by sequestering needed iron. By 1977, production of at least 66 different antibiotics had been reported in different strains of Bacillus (Katz and Demain, 1977, *Bacteriol. Rev.* 41:449–474). Furthermore, some strains of *Bacillus cereus* and *B. thuringiensis* have the ability to produce auxiliary proteins; compounds that enhance the activity of bacterial pesticides. (Warren et al. 1998, U.S. Pat. No. 5,770,696).

Several strains of *Bacillus cereus* have been patented for their antifungal properties against plant pathogens (Handelsman et al. 1996, U.S. Pat. No. 5,552,138; Handelsman et al. 1997, U.S. Pat. No. 5,700,462; Handelsman et al. 2000, U.S. Pat. No. 6,034,124). The antibiotics zwittermicin and kanosamine are commonly produced by strains of *Bacillus cereus* (Handelsman, supra). Production of the antibiotic iturin A by a strain of *Bacillus amyloliquefaciens* was demonstrated for control of fungi that cause disease in animals (Tanaka et al. 1995, U.S. Pat. No. 5,470,827), but it is not known to use *Bacillus amyloliquefaciens* for control of fungi in agriculture. An abundant amount of research has been published on the fungal biocontrol activity of diverse strains of *Bacillus subtilis*, and their diverse antifungal antibiotics (Asaka and Shoda, 1996, *Appl. Env. Microbiol.* 62(11):4081–4085; Guelder et al. 1988, *J. Agric. Food Chem.* 36:366–370; Mckeen et al. 1986, *Phytopathology* 76(2):136–139). Fungal biocontrol efficiency varies widely among strains of *Bacillus subtilis* as demonstrated in a study where twenty-one strains of *Bacillus subtilis* were evaluated simultaneously against fourteen fungal pathogens (Utkhede and Sholberg, 1986, *Can. J Microbiol.* 32:963–967). Various strains of *Bacillus subtilis* with antifungal activity have been patented (Pusey and Wilson, 1988, U.S. Pat. No. 4,764,371; Bacon and Hinton, 1999, U.S. Pat. No. 5,994,117; Heins et al., 2000, U.S. Pat. No. 6,103,228).

While various biocontrol agents for control of pathogenic fungi are known in the art, available biocontrol products cover a small range of crops and have a very small share of the crop protection market. (Whipps, 1994, Advances in biological control in protected crops, Brighton Crop Prot. Conf. Pest Dis. 9B:1259–1264). Present fungal biocontrols are not perceived as effective, reliable, and cost-efficient for present large-scale agricultural use. Poor activity has been linked to poor colonization due to competition by microorganism, or release of plant exudates which selectively encourage or prevent colonization by specific groups of microorganisms (Berger et al. 1996, *Phytopathology* 86(5):428–433). In contrast to fungicides, biocontrol agents often lack activity at higher pathogen concentrations (Whipps, supra). The approach taken by most researchers is the use of a characterized single strain biocontrol agent. One drawback to the single strain biocontrol approach is that environmental conditions in agriculture fields are highly dynamic and therefore not always optimal for a single biocontrol strain. So it can be difficult or impossible for this single strain to colonize the foliage, roots and soil around the roots, and maintain populations at levels high enough to suppress the growth of fungal pathogens during the whole crop cycle. On the other side of the spectrum of biological diversity, uncharacterized multi-species biocontrol products such as compost teas have proven unreliable, probably because of uncontrollable changes in the species composition of the microbial community. A biocontrol approach, however, using a combination of strains with antifungal activities can be more effective than a single strain biocontrol agent as there are more chances of successful colonization and more antifungal mechanisms operating simultaneously. A few products that include different bacteria strains for biocontrol of fungal diseases in plants have been patented (Cuero et al., 1998, U.S. Pat. No. 5,830,459; Drahos and Miller, 2001, U.S. Pat. No. 6,194,193; Ocamb et al., 2000, U.S. Pat. No. 6,133,196). There exists a continuing need for alternative biocontrol compositions and methods.

All documents or publications cited herein are incorporated by reference in their entirety, to the extent not inconsistent with the explicit teachings set forth herein.

BRIEF SUMMARY OF THE INVENTION

This invention relates to a novel approach to reduce or suppress the incidence or severity of fungal-induced diseases in plants, which, in a preferred embodiment, consists of a synergistic combination of novel Bacillus strains (*Bacillus cereus* "B1," *Bacillus amyloliquefaciens* "B2," *Bacillus cereus* "B3," and *Bacillus subtilis* "B4") that inhibits the growth of fungal pathogens. To this end, the biocontrol activity of the blend is more consistent, and provides biocontrol over a wider range of fungal pathogens, than that obtained by the individual components of the blend, which themselves are novel and can be used as biocontrol agents.

In a preferred embodiment, the treatment composition of the present invention consists of a unique combination of bacteria, specifically strains *Bacillus cereus* "B 1," *Bacillus amyloliquefaciens* "B2," *Bacillus cereus* "B3," and *Bacillus subtilis* "B4."

Accordingly, it is an object of the present invention to provide evidence of suppression of fungal diseases by a biocontrol product on different food crop plants.

Further objects and advantages of the present invention will become apparent by reference to the following detailed disclosure of the invention and appended photographs.

DEPOSIT OF THE MICROORGANISMS

*Bacillus cereus* "B1," *Bacillus amyloliquefaciens* "B2," *Bacillus cereus* "B3," and *Bacillus subtilis* "B4" have been deposited under the provisions of the Budapest Treaty with the Agriculture Research Culture Collection (NRRL) having a place of business at 1815 N. University Street, Peoria, Ill. 61604, U.S.A. The accession numbers at NRRL are: *Bacillus cereus* "B1" (NRRL B-30517), *Bacillus amyloliquefaciens* "B2" (NRRL B-30518), *Bacillus cereus* "B3" (NRRL B-30519), and *Bacillus subtilis* "B4" (NRRL B-30520).

BRIEF DESCRIPTION OF THE DRAWINGS

FIG. 1. Photograph of bell pepper plants either treated (plants on the right side, labeled "*Phytophthora+Bacillus*") or non-treated with BP01 (plants in the center, labeled as "Phytophthora solo") 20 days after inoculation with *Phytophthora capsici*. Control treatment (plants on the left, labeled "testigo") was not inoculated with *Phytophthora capsici* or BP01. Example 4.

FIG. 2. Photograph of control jalapeño pepper field (three beds labeled "testigo"), 94 days after planting in Example 5, trial 1.

FIG. 3. Photograph of jalapeño pepper field (three beds labeled "Phytophthora solo"), 94 days after planting and 32 days after inoculation with *Phytothora capsici* in Example 5, trial 1.

FIG. 4. Photograph of jalapeño pepper field treated with BP01 (three beds labeled "Phytophthora+BP01"), 94 days after planting and 32 days after inoculation with *Phytophthora capsici* in Example 5, trial 1.

FIG. 5. Photograph of control jalapeño pepper field (three beds labeled "testigo"), 92 days after planting in Example 5, trial 2.

FIG. 6. Photograph of jalapeño pepper field (three beds labeled "*Phytophthora capsici* solo"), 92 days after planting and 40 days after inoculation of *Phytothora capsici* in Example 5, trial 2.

FIG. 7. Photograph of jalapeño pepper field treated with BP01(three beds labeled "*Phytothora capsici Bacillus*"), 92 days after planting and 40 days after inoculation with *Phytothora capsici* in Example 5, trial 2.

DETAILED DISCLOSURE OF THE INVENTION

The present invention provides a novel approach of biocontrol that exerts suppression over species of fungi responsible for diseases in plants.

Biocontrol Product "BP00" is a blend of three strains of Bacillus (*Bacillus cereus* "B1," *Bacillus amyloliquefaciens* "B2," and *Bacillus cereus* "B3"). Biocontrol Product "BP01" is a blend of four strains of Bacillus (*Bacillus cereus* "B1," *Bacillus amyloliquefaciens* "B2," *Bacillus cereus* "B3," and *Bacillus subtilis* "B4"). These bacterial strains may be isolated in substantially pure cultures. For purposes of this disclosure, "substantially pure" culture means a culture of a bacteria strain containing no other bacterial species in quantities sufficient to interfere with replication of the culture or to be detectable by normal bacteriological techniques. "Isolated" when used in connection with the organisms and cultures described herein includes not only a substantially pure culture, but also any culture of organisms which is grown or maintained other than as it is found in nature. One may obtain mutants or derivatives of the strains that constitute BP00 or BP01, or antimicrobial materials derived from these strains or derivatives or mutants thereof, that also provide biological control comparable to that provided by BP00 and BP01. Further, each individual strain (B1, B2, B3, or B4) or any combination of these strains can also provide fungal biocontrol, for example, as demonstrated in Examples 2 and 3 with formulation BP00, a blend of three strains of Bacillus: *Bacillus cereus* "B1," *Bacillus amyloliquefaciens* "B2," and *Bacillus cereus* "B3." It will also be clear that addition of other microbial strains or complex microbial products to BP01, or any of the strains that constitute BP01, will also provide biological control and will not constitute a substantially different biocontrol product.

Each one of the strains that constitute BP01 is preferably cultured individually using conventional liquid or solid fermentation techniques. The four strains that constitute BP01 are capable of producing spores. BP01 can be made with vegetative cells or spores or combinations thereof. Once the cells have reached satisfactory density sporulation, the four fermentation products are blended together to yield BP01.

Fungal antagonistic activity occurs when the four strains are present, no matter the proportion of the different bacterial constituents. However, in a particularly preferred embodiment, B1, B2, B3, and B4 are present in roughly equal amounts.

Compositions within the present invention can be formulated as: aqueous suspensions; stabilized liquid suspensions; emulsifiable concentrates; capsules; soluble or wettable powders; aqueous flowables; dry flowables; wettable granules; wettable dispersible granules; and the like, as is known to those skilled in the art. BP01 can also be incorporated into fertilizers, soil, or foliar additives. Other suitable formulations will be readily apparent to those skilled in the art.

Soil, seeds, plantules or plants can be treated with BP01. The biocontrol agent can be applied manually or by means of machines (sprayers) or irrigation systems. It is impossible to predict the occurrence of the pathogen in a field crop. Therefore, several applications of BP01 are desirable for optimal biocontrol activity throughout crop cycle. Best results are achieved when BP01 is added frequently (one to ten times a month). Inoculation of plants with BP01 is recommended prior to pathogen exposure, whenever possible.

An application protocol that has been successfully tested in field operations consists of treating the plantules with BP01 in the nursery one or two weeks before planting at a concentration of $10^4$ to $10^7$ colony forming units (cfu) per milliliter. Best results are obtained in nurseries when a diluted solution of BP01 ($10^3$ to $10^4$ cfu per ml) is sprayed daily during the whole nursery stay. When transplanting, the plantules are submerged in a solution of BP01 at planting (root dip; $10^3$ to $10^7$ cfu per ml) or planted and irrigated afterwards with a solution of BP01 ($2\times10^{11}$ to $1\times10^{12}$ cfu per hectare; $8\times10^{10}$ to $4\times10^{11}$ cfu per acre). For optima BP01 should be applied regularly (e.g., one to ten times a month) during the growing season. BP01 should be applied to the field early in the morning or late in the afternoon to avoid bacterial mortality from solar activity. Application of pesticides or substances with antibacterial activity should be avoided (unless previously tested in a bioassay) as these substances can destroy the bacteria cells that constitute BP01. If a pesticide is required, BP01 should be reapplied one week after pesticide application. Organic and/or inorganic fertilizers can be added simultaneously with BP01 to help build populations of BP01 in the foliage, roots, and soil.

The following examples are provided to illustrate the invention. These examples are not to be construed as limiting. Example 1 describes the identification of the four Bacillus strains that constitute BP01. Examples 2 and 3 describe the in vitro evaluation of antagonism by Bacillus formulations to fungal pathogens. Example 4 describes greenhouse testing of BP01. Example 5 describes field trials carried out at Rancho Los Melendez (Km 18 highway Chihuahua-Aldama) at the State of Chihuahua, Mexico. The pathogen was intentionally inoculated at very high concentrations in the field for these trials. Example 6 describes a field trial carried out at Agricola Tarriba, located at La Cruz de Elota, State of Sinaloa, Mexico, where disease caused by *Phytothora capsici* is a common occurrence.

Following are examples which illustrate procedures for practicing the invention. These examples should not be construed as limiting. Unless otherwise noted, all percentages are by weight and all solvent mixture proportions are by volume.

EXAMPLE 1

Characterization of Strains

Strains were characterized by two methods, fatty acid methyl ester profile (FAME) (Tables 1 to 4) and genetic analysis based on sequencing all or part of the 16S rRNA gene (Table 5). Both tests were carried out by Accugenix, a division of Acculab, 223 Lake Drive, Newark, Del. 19702.

TABLE 1

Fatty acid methyl ester profile for Strain B1

| Name | % |
|---|---|
| 12:0 ISO | 0.33 |
| 13:0 ISO | 7.86 |
| 13:0 ANTEISO | 0.69 |
| 14:0 ISO | 2.93 |
| 14:0 | 3.58 |
| 15:0 ISO | 38.66 |
| 15:0 ANTEISO | 4.07 |
| 15:0 | 0.54 |
| 16:1 ω7C alcohol | 0.73 |
| Sum in feature 2 | 2.42 |
| 16:0 ISO | 4.27 |
| Sum in feature 3 | 9.69 |
| 16:0 | 4.42 |
| 15:2 OH | 0.76 |
| ISO 17:1 ω10C | 2.88 |
| ISO 17:1 ω5C | 5.68 |
| 17:1 | 0.88 |

TABLE 1-continued

Fatty acid methyl ester profile for Strain B1

| Name | % | | |
|---|---|---|---|
| ANTEISO A | | | |
| 17:0 ISO | 8.63 | | |
| 17:0 ANTEISO | 0.98 | | |
| Summed feature 2 | 2.42 | 12:0 ALDE<br>16:1 ISO I/14:0 3OH | Unknown 10.928<br>14:0 3OH/16.1 ISO I |
| Summed feature 3 | 9.69 | 16:1 ω7C/15 ISO 2OH | 15:0 ISO 2OH/16:1ω7C |
| Data base similarity index: *Bacillus cereus* | | | 0.863 |

TABLE 2

Fatty acid methyl ester profile for Strain B2

| Name | % | | |
|---|---|---|---|
| 13:0 ISO | 0.35 | | |
| 14:0 ISO | 0.63 | | |
| 14:0 | 1.83 | | |
| 15:0 ISO | 28.64 | | |
| 15:0 ANTEISO | 39.56 | | |
| 15:0 | 1.07 | | |
| 16:1 ω7C alcohol | 8.39 | | |
| 16:0 ISO | 1.14 | | |
| 16:1 ω11C | 2.66 | | |
| 16:0 | 7.59 | | |
| ISO 17:1 ω10C | 1.84 | | |
| Sum in feature 4 | 0.73 | | |
| 17:0 ISO | 6.64 | | |
| 17:0 ANTEISO | 6.66 | | |
| 18:0 | 0.26 | | |
| Summed feature 4 | 0.73 | 17:1 ISO I/ANTEIB | 17:1 ANTEISO B/1 I |
| Data base similarity index: *Bacillus amyloliquefaciens* | | 0.447 | |

TABLE 3

Fatty acid methyl ester profile for Strain B3

| Name | % |
|---|---|
| 12:0 ISO | 0.33 |
| 12:0 | 0.27 |
| 13:0 ISO | 7.15 |
| 13:0 ANTEISO | 6.78 |
| 14:0 ISO | 3.02 |
| 14:0 | 3.85 |
| 15:0 ISO | 37.64 |
| 15:0 ANTEISO | 4.43 |
| 15:0 | 0.48 |
| 16:1 ω7C alcohol | 0.73 |
| Sum in feature 2 | 2.33 |
| 16:0 ISO | 4.68 |
| 16:1 ω11C | 0.35 |
| Sum in feature 3 | 9.85 |
| 16:0 | 4.76 |
| 15:2 OH | 0.79 |
| ISO 17:1 ω10C | 2.63 |
| ISO 17:1 ω5C | 5.31 |
| 17:1 ANTEISO A | 0.94 |
| 17:0 ISO | 8.56 |

TABLE 3-continued

Fatty acid methyl ester profile for Strain B3

| Name | % | | |
|---|---|---|---|
| 17:0 ANTEISO | 1.14 | | |
| Summed feature 2 | 2.33 | 12:0 ALDE<br>16:1 ISO I/14:0 3OH | Unknown 10.928<br>14:0 3OH/16.1 ISO I |
| Summed feature 3 | 9.85 | 16:1 ω7C/15 ISO 2OH | 15:0 ISO 2OH/16:1ω7C |
| Data base similarity index: *Bacillus cereus* | | 0.832 | |

TABLE 4

Fatty acid methyl ester profile for Strain B4

| Name | % | | |
|---|---|---|---|
| 13:0 ISO | 0.35 | | |
| 14:0 ISO | 1.14 | | |
| 14:0 | 0.69 | | |
| 15:0 ISO | 30.30 | | |
| 15:0 ANTEISO | 38.48 | | |
| 15:0 | 0.44 | | |
| 16:1 ω7C alcohol | 0.44 | | |
| 16:0 ISO | 2.23 | | |
| 16:1 ω11C | 1.33 | | |
| Sum in feature 3 | 0.30 | | |
| 16:0 | 3.59 | | |
| ISO 17:1 ω10C | 1.37 | | |
| Sum in feature 4 | 0.60 | | |
| 17:0 ISO | 9.84 | | |
| 17:0 ANTEISO | 7.94 | | |
| 18:1 ω7C | 0.68 | | |
| 18:0 | 0.28 | | |
| Summed in feature 3 | 0.30 | 16:1 ω7C/15 iso 2 OH | 15:0 ISO 2 OH/16:1ω7c |
| Summed in feature 4 | 0.60 | 17:1 ISO I/ ANTEI B | 17:1 ANTEISO B/i I |
| Data base similarity index: *Bacillus subtilis* | | 0.728 | |

TABLE 5

| Genetic analysis Strain Analysis | | Identification | % difference with closest match |
|---|---|---|---|
| B1 | 500 bp ID* | *Bacillus cereus* | 0 |
| B2 | 1500 bp ID | *Bacillus amyloliquefaciens* | 0.19 |
| B3 | 500 bp ID* | *Bacillus cereus* | 0 |
| B4 | 1500 bp ID | *Bacillus subtilis* | 0.1 |

*1500 bp ID was not carried out for strains B1 and B3 due to repeated PCR failures with these strains.

EXAMPLE 2

Fully grown cultures of *Phytophthora cinnamomi* on half concentration potato dextrose agar (PDA 1/2) and V8C agar (20 g agar, 4 g $CaCO_3$, 200 ml filtered V8 juice in one liter of distilled water) were cut in one square centimeter sized pieces with a flamed scalpel and transferred to the center of agar plates of the same respective media from which the inoculums originated. Cultures of *Bacillus cereus* "B1," *Bacillus amyloliquefaciens* "B2," *Bacillus cereus* "B3," and *Bacillus subtilis* "B4" were grown overnight in trypticase soy broth at 25–28° C. BP00 was prepared by mixing in a test tube equal amounts of B1, B2, and B3. BP01 was prepared by mixing in a test tube equal volumes of B1, B2, B3, and B4. Samples of 20 micro liters of each independent strain and BP01 were placed on top of the agar at a distance of 1.5 centimeters from the fungi. Two plates were set per treatment. Control cultures inoculated with *P. cinnamomi* were left bacteria-free to determine fungal growth. The plates were incubated at 25–28° C. for two weeks. Typical fungal inhibition consisted of a zone of no growth of the pathogen around the bacteria. The zone size was measured in millimeters. An average inhibition zone size was calculated from the two replicate readings and presented in Table 6.

TABLE 6

In-Vitro growth inhibition of *P. cinnamomi* by individual bacterial components of BP01 and by BP01 on two different culture media.

(Zone test, measured in millimeters)

| Biocontrol agent | PDA ½ | V8C |
|---|---|---|
| *Bacillus cereus* (B1) | 4 | 2 |
| *Bacillus amyloliquefaciens* (B2) | 4 | 3 |
| *Bacillus cereus* (B3) | 3 | 3 |
| *Bacillus subtilis* (B4) | 6 | 5 |
| BP00 (B1, B2, B3) | 7 | 4 |
| BP01 (B1, B2, B3, B4) | 9 | 7 |

EXAMPLE 3

A standard agar diffusion assay was set up as in Example 1, this time using cultures of Botrytis spp., Verticillum spp. and Rizoctonia spp. on PDA 1/2 and Fusarium spp., Monilinia spp., *Phytophthora capsici, P. cinnamomi, P. citricola, P. citrophthora*, and *P. parasitica* on V8C agar. Biocontrol agents BP00 and BP01 were evaluated. Same methods were used as in Example 1. Two replicates were run per treatment. Average values of both replicates are presented in Table 7.

TABLE 7

In Vitro growth inhibition of fungal plant pathogens by BP00 and BP01.

(Zone test, in millimeters)

| Pathogen | Host | BP00 | BP01 |
|---|---|---|---|
| Botrytis. spp. | lettuce | 2 | 4 |
| Fusarium spp. | tomato | 5 | 6 |
| Monilinia spp. | peach | 5 | 7 |
| *Phytophthora capsici* | pepper | 4 | 6 |
| *Phytophthora cinnamomi* | avocado | 6 | 9 |
| *Phytophthora citricola* | avocado | 6 | 8 |
| *Phytophthora citrophthora* | citrus | 11 | 11 |
| *Phytophthora parasitica* | citrus | 3 | 7 |
| Rizoctonia spp. | turf | 5 | 5 |
| Verticillum spp. | strawberry | 3 | 5 |

EXAMPLE 4

Peat moss was steam sterilized in polypropylene bags and transferred to 300 ml nursery pots. *Phytothora capsici* was grown in 20 ml V8C media for 7 to 8 days (till complete coverage of agar surface). The agar was cut in 4 pieces with a flamed scalpel, and each piece was placed for two days in a Petri dish with sterile water to induce sporangia and zoospore production. 62.5% of the contents of a Petri dish were suspended in one liter of sterile water using a conventional blender. 40 ml of this suspension were inoculated into each pot, except for control treatments. The four strains constituting BP01 were grown individually until spore formation. The fermentation products were blended together and 20 ml of this suspension at $1\times10^8$ cfu was added per pot ($6\times10^6$ cfu per ml of soil). Bell pepper plantules grown for 4 weeks had between 3 and 4 leaves at the moment of transplant. Phytophthota and BP01 were added simultaneously to the sterilized peat moss. Bell peppers were planted just after the inoculation. The percentage of disease incidence was determined on days 4, 6, 8, 10 and 12 after planting. Twenty pots were set per treatment. Results are presented in Table 8 and FIG. 1.

TABLE 8

Percent incidence of root rot caused by *Phytophthora capsici* and its biocontrol by BP01 in bell peppers

| | % incidence | | | | |
|---|---|---|---|---|---|
| | day 4 | day 6 | day 8 | day 10 | day 12 |
| Control | 0 | 0 | 0 | 0 | 0 |
| *Phytophthora capsici* | 25 | 60 | 95 | 100 | 100 |
| *Phytophthora capsici* + BP01 | 0 | 5 | 10 | 10 | 30 |

EXAMPLE 5

Figure 2:
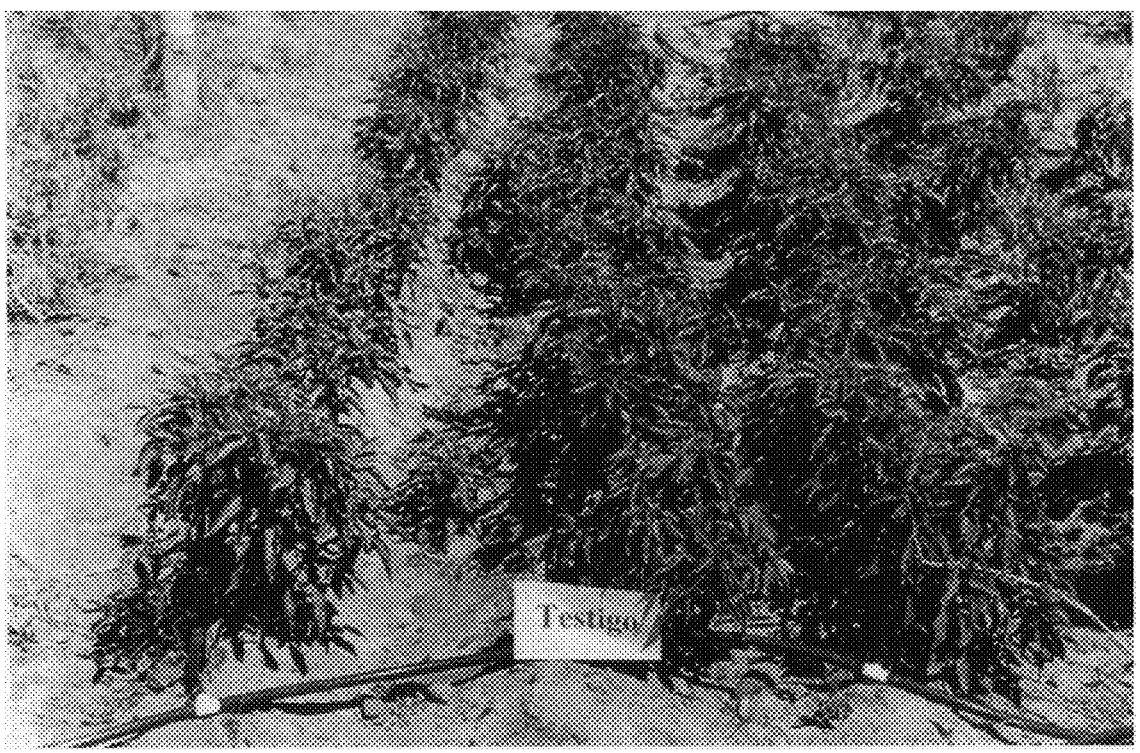
Figure 3:
Figure 4:
Figure 5:
Figure 6:
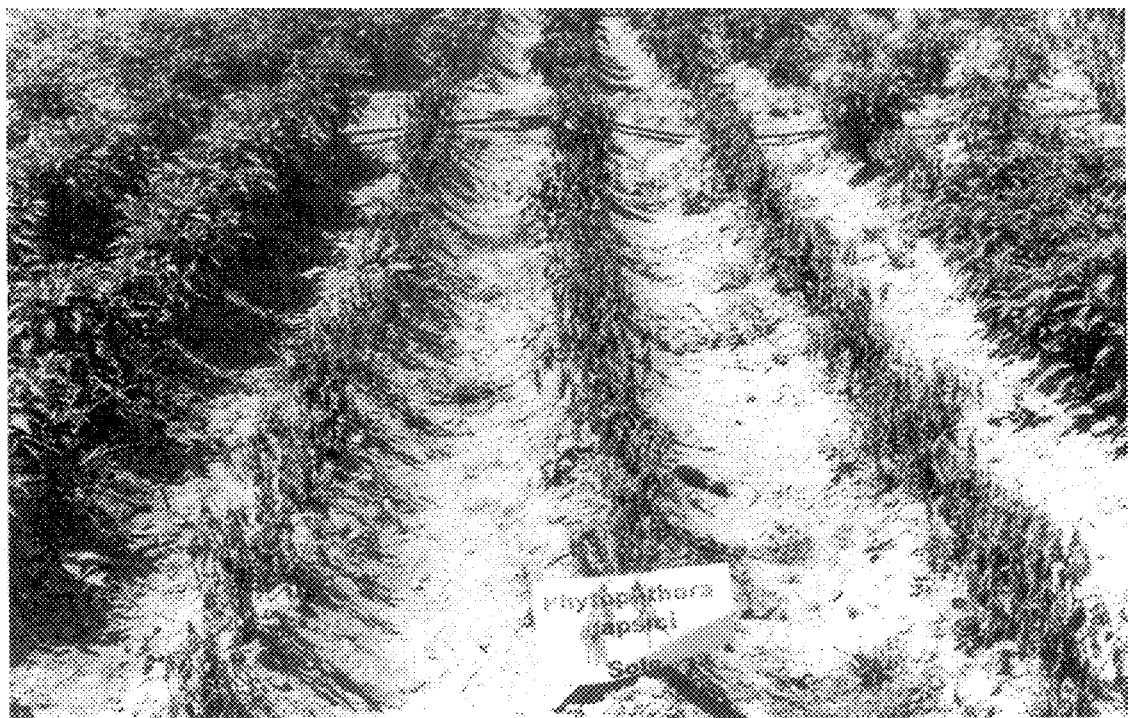
Figure 7:

Biocontrol field trial of *Phytothora capsici* by BP01 in jalapeño peppers (Mitla). A field in Aldama, Chihuahua (Mexico) with slightly alkaline sandy loam soil and low organic matter content was used for this trial. The soil was amended with a 150-80-0 urea-based fertilizer. Seven-meters-long beds were built every 80 cm. Jalapeño peppers seeds were planted in nursery trays and grown for 5 weeks; then were planted at a density of 3 plants per meter. The field was flood irrigated before planting, at planting, and then every 10 days for a period of two months, then was drip-irrigated twice a week, at a rate of 3 liters per drip hole per irrigation. Weeding was carried out manually every two weeks. Three treatments were set: untreated control, treatment with inoculated pathogen (*Phytophthora capsici*) and treatment with both inoculated pathogen (*Phytophthora capsici*) and biocontrol agent BP01. BP01 was applied 8 times at a rate of 2 liters per hectare (0.2 gallons per acre). BP01 had a concentration of $1\times10^{11}$ cfu per liter ($3.785\times 10^{11}$ cfu per gallon), so every application consisted of $2\times10^{11}$ cfu per hectare ($7.6\times10^{10}$ cfu per acre). BP01 was applied on days 48, 51, 55, 58, 62, 65, 69, and 72 after planting. *Phytophthora capsici* was prepared as described in Example 3, however this time the fungal contents of three Petri dishes were resuspended in one liter of water and 100 ml were inoculated per bed. *Phytothora capsici* was inoculated in the field on day 62 after planting, the same day of the fifth application of BP01. Three beds were set as replicates per treatment. The experiment was run twice. Thirty-two days after the inoculation of the pathogen (day 94 after planting) percent incidence of disease was determined. Results of the first experimental run are presented in Table 9 and FIG. 2 (control plot, labeled 'testigo'), 3 (plot inoculated with *Phytophthora capsici*, labeled "Phytophthora solo") and 4 (plot inoculated with *Phytophthora capsici* and treated with BP01, labeled "Phytophthora+BP01"). Results of the second run are presented in FIG. 5 (control plot, labeled "testigo:), 6 (plot inoculated with *Phytophthora capsici*, labeled "Phytophthora solo") and 7 (plot inoculated with *Phytothora capsici* and treated with BP01, labeled "Phytophthora+BP01").

TABLE 9

Percent incidence of root rot caused by *Phytophthora capsici* and its biocontrol by BP01 in field trials with Jalapeño peppers.

| | Days after inoculation of pathogen | | | |
|---|---|---|---|---|
| Treatment | 8 | 16 | 24 | 32 |
| Control | 0 | 0 | 0 | 0 |
| *Phytophthora capsici* | 2.3 | 13.3 | 28.9 | 35.5 |
| *Phytophthora capsici* + BP01 | 1.7 | 1.7 | 1.7 | 3.4 |

EXAMPLE 6

Biocontrol field trial of naturally occurring *Phytothora capsici* by BP01 in Commandant variety bell peppers. The trial was carried out at the farm Ebano, property of Agricola Tarriba, located at La Cruz de Elota, State of Sinaloa, Mexico. Root rot caused by *P. capsici* is a common occurrence in this farm. Twelve beds 100 meters (328 feet) in length were used for the test. Six beds were set per treatment. The beds were randomly selected and separated in pairs. Each pair of beds was considered a replicate and three pairs of beds were set per treatment. Two treatments were evaluated, a control treatment and a BP01 treatment. The field was set up with drip irrigation lines, with independent valves for each bed so that BP01 could be applied to treated beds through the irrigation system.

BP01 applications were carried out weekly, for eight weeks, starting on day 25 after planting. The volume of BP01 applied each time was 4 liters per hectare. BP01 was prepared at a concentration of $1\times10^{11}$ cfu per liter ($3.785\times 10^{11}$ cfu per gallon), so the amount of BP01 added at each application is $4\times10^{11}$ cfu per hectare ($1.6\times10^{11}$ cfu per acre). The amount of BP01 inoculated each time to the six beds was diluted in 400 liters of water and applied in 15 minutes. Total amount of BP01 added during the crop cycle was 32 liters per hectare (3.4 gallons per acre).

Percent mortality was determined for each bed by calculating the proportion of dead plants from the initial number of plants (Table 10). All beds had an area that was holding water, so the percent incidence of root rot was determined for each bed in this flooded area (Table 11). Production of peppers under both treatments was determined in four size categories (extra-large, large, medium and small) using the criteria established by commercial packing companies (Table 12).

TABLE 10

Percent incidence of root rot caused by *Phytophthora capsici* and its biocontrol by BP01 in bell peppers

| Treatment | % incidence |
|---|---|
| Control | 8.3 |
| BP01 | 2.4 |

TABLE 11

Percent incidence of root rot caused by *Phytophthora capsici* and its biocontrol by BP01 in flooded areas

| Treatment | % incidence |
|---|---|
| Control | 22.1 |
| BP01 | 7.8 |

TABLE 12

Production for different size categories of bell peppers under BP01 treatment

| Treatment | Extra large | Large | Medium | Small | Total |
| --- | --- | --- | --- | --- | --- |
| Control | 750 | 825 | 1554 | 900 | 4029 |
| BP01 | 918 | 930 | 1712 | 915 | 4475 |

Although this year had a low incidence of disease, there was a statistically significant difference between untreated and BP01 treated fields both in percent incidence of disease and in total production.

Inasmuch as the preceding disclosure presents the best mode devised by the inventor for practicing the invention and is intended to enable one skilled in the pertinent art to carry it out, it is apparent that methods incorporating modifications and variations will be obvious to those skilled in the art. As such, it should not be construed to be limited thereby but should include such aforementioned obvious variations and be limited only by the spirit and scope of the following claims.

What is claimed is:

1. An isolated culture of a bacterial strain, said bacteria strain selected from the group consisting of *Bacillus cereus* strain B1, having accession number NRRL B-30517; *Bacillus amyloliquifaciens* strain B2, having accession number NRRL B-30518; *Bacillus cereus* strain B3, having accession number NRRL B-30519; and *Bacillus subtilis* strain B4, having accession number NRRL B-30520.

2. An isolated culture according to claim 1, wherein said bacteria is *Bacillus cereus* strain B1, said strain having accession number NRRL B-30517.

3. An isolated culture according to claim 1, wherein said bacteria is *Bacillus amyloliquifaciens* strain B2, said strain having accession number NRRL B-30518.

4. An isolated culture according to claim 1, wherein said bacteria is *Bacillus cereus* strain B3, said strain having accession number NRRL B-30519.

5. An isolated culture according to claim 1, wherein said bacteria is *Bacillus subtilis* strain B4, said strain having accession number NRRL B-30520.

6. A biocontrol composition comprising in combination, at least two bacterial strains selected from the group consisting of *Bacillus cereus* strain B1, having accession number NRRL B-30517; *Bacillus amyloliquifaciens* strain B2, having accession number NRRL B-30518; *Bacillus cereus* strain B3, having accession number NRRL B-30519; and *Bacillus subtilis* strain B4, having accession number NRRL B-30520.

7. A biocontrol composition according to claim 6, comprising in combination: *Bacillus cereus* strain B1, having accession number NRRL B-30517; *Bacillus amyloliquifaciens* strain B2, having accession number NRRL B-30518; and *Bacillus cereus* strain B3, having accession number NRRL B-30519.

8. The biocontrol composition of claim 7, wherein said composition comprises substantially equal amounts of each of said bacterial strains.

9. The biocontrol composition of claim 7, wherein said bacterial strains are in spore form.

10. The biocontrol composition of claim 7, further comprising *Bacillus subtilis* strain B4, having accession number NRRL B-30520.

11. The biocontrol composition of claim 10, wherein said composition comprises substantially equal amounts of each of said bacterial strains.

12. The biocontrol composition of claim 10, wherein said bacterial strains are in spore form.

13. A method of biocontrol conferring improved pathogen resistance to an object comprising the steps of:

a) obtaining a biocontrol composition according to claim 7; and b) applying said biocontrol composition to the object, thereby conferring improved pathogen resistance to said object as compared to the object before applying said biochemical composition.

14. The method of claim 13 further comprising applying said biocontrol composition to said object prior to pathogen exposure.

15. The method of claim 13 wherein said object is selected from the group consisting of seeds, plants, plantules, soil, and planting media.

16. The method of claim 13 further comprising applying said biocontrol composition from one to ten times a month.

* * * * *

UNITED STATES PATENT AND TRADEMARK OFFICE
CERTIFICATE OF CORRECTION

PATENT NO. : 6,589,524 B1 Page 1 of 1
DATED : July 8, 2003
INVENTOR(S) : Philippe Douillet It is certified that error appears in the above-identified patent and that said Letters Patent is hereby corrected as shown below:

Column 5,
Lines 4 and 5, "For optima BP01" should read -- For optimal results, BP01 --.
Line 44, "Lake Drive, Newark, Del. 19702." should read -- Lake Drive, Newark, DE 19702. --.

Column 8,
Line 42, Table 7, "(Zone test, in millimeters)     -- BP00     BP01
                     BP00      BP01" should read    (Zone test, in millimeters) --.

Column 9,
Line 32, "80 cm. Jalapeñio peppers" should read -- 80 cm. Jalapeño peppers --.

Signed and Sealed this

Eighteenth Day of November, 2003

JAMES E. ROGAN
*Director of the United States Patent and Trademark Office*